(12) United States Patent
Wang et al.

(10) Patent No.: US 11,168,263 B2
(45) Date of Patent: Nov. 9, 2021

(54) APPARATUS AND METHOD FOR PREPARING ETHYLENE AND/OR ACETYLENE USING HYDROCARBON

(71) Applicant: Tsinghua University, Beijing (CN)

(72) Inventors: Tiefeng Wang, Beijing (CN); Jiajia Luo, Beijing (CN); Jinfu Wang, Beijing (CN); Tianpeng Li Zhou, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 0 days.

(21) Appl. No.: 17/193,285

(22) Filed: Mar. 5, 2021

(65) Prior Publication Data

US 2021/0189255 A1 Jun. 24, 2021

Related U.S. Application Data

(63) Continuation of application No. PCT/CN2018/114996, filed on Nov. 12, 2018.

(51) Int. Cl.
*C10G 9/20* (2006.01)
*B01J 19/24* (2006.01)
*B01J 19/26* (2006.01)
*C07C 4/04* (2006.01)
(Continued)

(52) U.S. Cl.
CPC .......... *C10G 9/206* (2013.01); *B01J 19/2415* (2013.01); *B01J 19/26* (2013.01); *C07C 4/04* (2013.01); *B01J 2219/00159* (2013.01); *C07C 11/04* (2013.01); *C07C 11/24* (2013.01)

(58) Field of Classification Search
CPC ........ C10G 9/206; C10G 9/36; B01J 19/2415; B01J 19/26; B01J 2219/00159; B01J 2208/00504; B01J 2219/00157; B01J 8/062; B01J 19/2425; C07C 4/04; C07C 11/04; C07C 11/24
See application file for complete search history.

(56) References Cited

U.S. PATENT DOCUMENTS 3,161,695 A * 12/1964 Goffinet, Jr. .............. C07C 4/04
585/539
7,291,761 B2 * 11/2007 Machhammer .......... B01J 8/025
585/658
2002/0081248 A1 6/2002 Boyer et al.

FOREIGN PATENT DOCUMENTS

| CN | 103030493 A | 4/2013 |
| CN | 103242122 A | 8/2013 |
| CN | 106854127 A | 6/2017 |

* cited by examiner

*Primary Examiner* — Randy Boyer
*Assistant Examiner* — Juan C Valencia
(74) *Attorney, Agent, or Firm* — IPRO, PLLC

(57) ABSTRACT

Equipment for producing ethylene and/or acetylene from hydrocarbons, including the reaction chamber (13), burner (11), common or separate fuel gas inlets (12) and oxygen inlets (18), preheating tubes (14), a gas distributor (15), cracking gas inlets (16), and a reaction product outlet (17); the gas distributor (15), which has multiple gas inlets and gas outlets, is arranged on the cross section of the reaction chamber (13), where the gas inlet is connected to the cracking gas inlet (16), and the gas outlet is connected to the preheating tube (14). The cracking gas is uniformly distributed through the gas distributor (15) and passed through the (Continued)

preheating tubes (14), which are hollow tubes; the opening at the other end of the hollow tube is close to or inserted into the combustion area of the gaseous fuel and oxygen.

18 Claims, 2 Drawing Sheets

(51) Int. Cl.
*C07C 11/04* (2006.01)
*C07C 11/24* (2006.01)

APPARATUS AND METHOD FOR PREPARING ETHYLENE AND/OR ACETYLENE USING HYDROCARBON

FIELD OF THE INVENTION

The present invention relates to the technical field of ethylene and/or acetylene production, and in particular to an apparatus for producing ethylene and/or acetylene by cracking hydrocarbons and a method of using the apparatus for producing ethylene and/or acetylene.

BACKGROUND OF THE INVENTION

Ethylene is one of the world's largest output chemical products and plays a very important role in the national economy. It is mainly used for the production of polyethylene, ethylene-propylene rubber, polyvinyl chloride, etc. At present, ethylene is mainly produced by steam cracking of naphtha of ethane in the industry. Acetylene is another very important basic chemical raw material, the downstream products of which are mainly vinyl chloride, vinyl acetate, 1,4-butadiene, etc. At present, acetylene is mainly produced by calcium carbide in China, while in the natural gas-rich regions in foreign countries acetylene is mainly produced by partial oxidation of natural gas.

Steam cracking is a process that uses a mixture of hydrocarbons and water to thermally crack at high temperature to produce ethylene. The advantage of this process is the high yield, while the disadvantages are high energy consumption and complex reactor structure. The reaction of the calcium carbide with water is used to produce acetylene. The advantages of this method is the high product purity and easy operation. However, the high energy consumption and severe environmental pollution are the disadvantages of this process.

Tubular cracking furnace is used to produce ethylene by water vapor cracking. Although there are different kinds of tube furnaces, from the structural point of view, they are composed of furnace tubes, tube racks, burners, furnace walls, and furnace racks, and they mainly consist of the convection section and radiation section. The scale-up of the tube furnace reactor is carried out by increasing the number of reaction tubes, resulting in a complicated reactor structure. For specific reactor structure, please refer to "Ethylene Plant Technology and Operation" edited by Wang Songhan et al. The reactor for partial oxidization of natural gas to acetylene is mainly divided into a mixer, a combustion nozzle, and a reaction chamber. The scale-up of the reactor is achieved by increasing the number of nozzles. For the specific reactor structure, please refer to the acetylene entry (DOI:10.1002/14356007.a01_097.pub4) written by Peter et al. from BASF in the book Ullmann Encyclopedia of Industrial Chemicals.

At present, most of the patents are for the improvement of the tubular cracking furnace, but there are few patents for the direct mixing of gaseous fuel combustion products with hydrocarbons as heat carriers. CN01145130.0 proposes an apparatus for producing ethylene by rapidly mixing supersonic heat carrier and hydrocarbons, but the reactor structure in this patent is complicated, which is not conducive to industrial application. The main problem is that the patent does not consider the problem of reactor scale-up. When the reactor is scaled up, it is difficult to mix the cracking gas and the heat carrier uniformly, so the reaction yield will be significantly reduced. U.S. Pat. No. 2,941,021 adopts the method of swirling injection of reaction material, adding the stirring effect in the mixing process of heat carrier and reaction material to intensify the mixing. There are two main problems in this apparatus: one is that near the central axis of the reactor, the stirring effect is weak and the mixing performance is not good; the other problem is that when the size of the reactor is scaled up, it is difficult to completely mix the heat carrier with the material simply by stirring the material through swirling injection. U.S. Pat. No. 4,256,565 uses the method of injecting the hydrocarbons that need to be cracked near the fuel nozzle to quickly mix the heat carrier generated by combustion and the injected hydrocarbons. Although this reactor structure can be scaled up by increasing the number of nozzles to solve the problem of scale-up of the reactor, the heat carrier generated by fuel combustion is not completely burned when mixed with hydrocarbons, and the residual oxygen will reduce the yield of ethylene/acetylene.

SUMMARY OF INVENTION

The invention provides a reaction apparatus for producing ethylene and/or acetylene from low carbon alkanes in view of defects in the prior art. The reaction apparatus has the advantages of simple structure, no scale-up effect, uniformly mixing of the heat carrier and the reaction material, high yield and selectivity of ethylene and/or acetylene, and the like.

According to a broad embodiment, the invention provides an apparatus for producing ethylene and/or acetylene from hydrocarbons, said apparatus comprising: reaction chamber, burner, common or separate gaseous fuel inlet and oxygen inlet, preheating tube, gas distributor, cracking gas inlet, and reaction product outlet; The reaction chamber is a cavity structure in which reaction raw materials are reacted; The burner, gaseous fuel inlet, oxygen inlet, cracking gas inlet, and reaction product outlet are arranged on the wall of the reaction chamber, and the pre-heating tube and the gas distributor are arranged in the reaction chamber; The gaseous fuel inlet is used to pass gaseous fuel into the reaction chamber; The oxygen inlet is used to pass oxygen into the reaction chamber; The burner is used to ignite the gaseous fuel and oxygen; The reaction product outlet is used to discharge the cracked product out of the reaction chamber; The inlet is used to pass cracking gas into the reaction chamber; The gas distributor is arranged on the cross section of the reaction chamber, and the gas distributor has a gas inlet and a gas outlet. The gas inlet is connected with the cracking gas inlet, and the gas outlet of the gas distributor is connected with the pre-heating row tube. The gas distributor is used to evenly distribute the cracking gas that enters through the cracking gas inlet on the cross section of the reaction chamber and pass it to the preheating tube. The preheating tube includes a plurality of hollow tubes with open ends. The opening at one end is connected with the gas outlet on the gas distributor, and the opening at the other end is in the combustion area of gaseous fuel and oxygen, which is used to feed the cracking gas evenly distributed by the gas distributor into the gaseous fuel and oxygen combustion area after preheating. During the cracking reaction, the reaction products are distributed around the hollow tubes and preheating the cracking gas within the tubes.

In the apparatus for producing ethylene and/or acetylene from hydrocarbon, the gas distributor is combined with the preheating tube so that the gas distribution and gas flow direction after the cracking gas enters the reaction chamber are significantly different from that in the traditional apparatus for producing ethylene and/or acetylene from hydrocarbon. First, the use of a gas distributor and hollow tubes allows the cracking gas that enters the reaction chamber from the cracking gas inlet to be diffused or evenly distributed on the cross section of the reaction chamber after passing through the gas distributor and the hollow tubes. Different from the traditional highly concentrated flow centered on the inlet of cracking gas, the benefits of uniform distribution of cracking gas are to make the cracking gas contact and mix with the heat carrier evenly, so as to make the subsequent cracking reaction more sufficient and uniform. Second, the preheating tubes connected with the gas distributor preheat the diffused and evenly distributed cracking gas and keep it evenly distributed, and then the preheated cracking gas is ejected from the hollow tubes into the heat carrier area formed by the combustion of gaseous fuel and oxygen for cracking reaction. The high-temperature cracking products are distributed around the hollow tubes, and the heat is transferred to the hollow tubes and the cracking gas that is continuously fed, thereby preheating the cracking gas.

The invention eliminates or even solves the problem of the scale-up effect of the traditional reaction chamber: in the prior art, when the reaction chamber is scaled up, the cracking raw materials and the heat carrier are mixed unevenly, resulting in a poor reaction performance and a significant decrease in yield. In the present invention, because the cracking gas is preheated and uniformly distributed using tubes, the cracking raw material hydrocarbons and the heat carrier are uniformly contacted and mixed, so that the yield is not affected by the scale-up of the reaction chamber.

It can be seen that the working process of the apparatus of the present invention is: the gaseous fuel and oxygen are injected into the reaction chamber through common or separate gaseous fuel inlet and oxygen inlet, and are ignited by a burner to form a heat carrier area around the combustion point; at the same time, the cracking gas enters the reaction chamber from the cracking gas inlet, and is then sent to the gas inlet of a gas distributor, and then goes from the gas outlet of the gas distributor to the preheating hollow tubes, and flows along the interior of the hollow tubes under the impact of the continuous flow of cracking gas. The cracking gas is heated by the high-temperature cracked products when flowing in the hollow tubes. When ejected from the other end of the hollow tube, the cracking gas enters the heat carrier area formed by the combustion of gaseous fuel and oxygen. The cracking gas is thermally cracked to form cracked products such as alkyne and alkene. The cracked product diffuses in the area around the hollow tubes. The high temperature of the cracked product heats the hollow tubes and the cracking gas continuously entering the tubes, and finally the cracked product exits the reaction chamber from the reaction product outlet. Therefore, the combination of the gas distributor and the preheating tubes makes the cracking gas hydrocarbons evenly distributed in the hollow tubes of the preheating tube. From the end of each hollow tube, heated cracking gas is ejected, and the ejected cracking gas is in contact with the heat carrier to form a cracking reaction point for the cracking gas, thereby forming multiple cracking reaction points in the reaction chamber. While the preheating tubes play the role of heating the cracking gas, the reaction is also scaled up, whereby the cracking gas channel uses multiple tubes, which can inject the cracking gas into the reactor and mix with the heat carrier. Through the method of number scale-up, the reactor can be scaled up without the problem of incomplete reaction and decreased yield due to the uneven contact between cracking gas and heat carrier, which occurs in the conventional reactor.

Further, the gas outlet of the gas distributor and the hollow tubes of the preheating tube connecting with the gas distributor are uniformly distributed on the cross section of the reaction chamber. The purpose of uniformly distributing the gas outlet of the gas distributor and the connected hollow tubes on the cross section of the reaction chamber is to form a uniform distribution of reaction points on the cross section of the reaction chamber. This will make the reaction more complete and uniform.

Furthermore, the gaseous fuel inlet and the oxygen inlet are arranged on the top of the reaction chamber, and the cracking gas inlet, the gas distributor and the preheating tube are arranged on the lower part of the reaction chamber. This is a preferred solution for the layout of the reaction chamber. The common and/or separate gaseous fuel inlet and oxygen inlet are set on the top of the reaction chamber, and the burner is also set on the top of the reaction chamber; the cracking gas inlet and gas distributor, and the preheating tube are arranged on the lower part of the reaction chamber. The reaction product outlet is arranged above the gas distributor. It can be seen that this is the layout of the reaction chamber in the embodiment where the cracking gas flows from the bottom to the top of the reaction chamber, and then it is injected from the upper end of the hollow tube into the combustion zone of the fuel gas and oxygen at the top of the reaction chamber. The cracking reaction of the cracking gas occurs at the top of the reaction chamber.

Furthermore, the gaseous fuel inlet and the oxygen inlet are arranged at the bottom of the reaction chamber, and the cracking gas inlet, the gas distributor and the preheating tube are arranged at the upper part of the reaction chamber. As an alternative to the above scheme of cracking gas flowing up from the bottom of the reaction chamber, the cracking gas inlet, the gas distributor and the preheating tube can be arranged at the upper part of the reaction chamber. The gaseous fuel inlet and the oxygen inlet can be arranged at the bottom of the reaction chamber. The reaction product outlet is set below the gas distributor. In this layout scheme of the reaction chamber, the cracking gas enters from the cracking gas inlet at the upper part of the reaction chamber and passes down through the gas distributor into the hollow tubes of the preheating tube, and is injected from the lower end of the hollow tubes into the combustion zone of gaseous fuel and oxygen at the bottom of the reaction chamber.

Further, as a scheme for the arrangement of gaseous fuel inlet and oxygen inlet in the apparatus of the present invention, the gaseous fuel inlet and oxygen inlet are the same common inlet, and the gaseous fuel and oxygen enter the reaction chamber through the same common inlet after being premixed.

Preferably, the apparatus of the present invention mentioned above in which the gaseous fuel inlet and the oxygen inlet are the same common inlet includes a mixer. The mixer is connected to the common inlet of the gaseous fuel inlet and the oxygen inlet for mixing the preheated gaseous fuel and oxygen, and then injected into the reaction chamber. In this preferred solution, the gaseous fuel and oxygen share the same common inlet, and the preheated gaseous fuel and oxygen premixed in the mixer are combusted as premixed flames. The scheme of premixing the preheated fuel gas and oxygen and then injecting them into the reaction chamber through the common inlet helps the gaseous fuel combust completely, but the problem of blowoff with combustion may occur.

Further, as an alternative to the same common inlet for the fuel gas and the oxygen, the fuel gas inlet and the oxygen inlet in the apparatus of the present invention are separate inlets, where the fuel gas and oxygen enter the reaction chamber through the separate fuel gas inlet and oxygen inlet, respectively. Fuel gas and oxygen are separately injected into the reaction chamber through their respective inlets to combust as non-premixed flames. This scheme has the advantage of simple operation, but requires a long time for complete combustion, resulting in an increase in reactor volume.

Further, the gas distributor in the apparatus of the present invention is of a plate shape and has a plurality of through holes connecting the gas inlet and the gas outlet. The through holes are evenly distributed on the entire plate surface of the cracking gas distributor, and each through hole is connected with a hollow tube. The gas distributor can be in various forms. The preferred distributor of the device in the invention is of a plate shape, which is arranged on the cross-section of the reaction chamber. The gas distributor divides the reaction chamber into upper and lower parts connected only by through holes on the plate surface. Because the gas distributor is parallel to the upper and lower bottom surface of the reaction chamber, the through holes connecting the gas inlet and gas outlet are evenly distributed on the surface. The through holes are evenly distributed on the surface of the plate, therefore the hollow tubes are evenly distributed on the cross section of the reaction chamber. The cracking gas passes through the gas inlet of the distributor, then exits through the gas outlet through the shortest path and enters the evenly distributed hollow tubes connected with the gas outlet. The advantages of this arrangement are as follows: there are hollow tubes in each area of the cross section of the reaction chamber, cracking gas in the hollow tubes is heated, and cracking reaction points are formed in each area of the cross section of the reaction chamber. There is no dead zone in the reaction chamber, and there is no problem of incomplete reaction caused by nonuniform cracking reaction.

Further, the shape of the through hole is a circle, a square, a triangle or a pentagon, and the cross-sectional shape of the hollow tube is a circle, a square or a triangle. Further, when the cross section of the hollow tube is circular, the diameter of the hollow tubes is in the range from 5 mm to 60 mm.

Further, according to the apparatus of the present invention, the common or separated fuel gas inlet (12) and oxygen inlet (18) are both distributed on the top or bottom of the reaction chamber (13), so that the fuel gas and oxygen combust to form a plurality of heat carrier regions in the cross section of the reaction chamber (13).

Further, a contraction is provided to each hollow tube for gas distribution and pressure adjustment. Preferably, the contraction is located near the gas distributor, which is more convenient to fabricate.

According to another aspect of the present invention, a method is also provided for producing ethylene and/or acetylene from hydrocarbon by using the apparatus mentioned above for producing ethylene and/or acetylene from hydrocarbon, including the following steps:

a) Injecting fuel gas and oxygen into the reaction chamber through the common or separate fuel gas inlet and oxygen inlet; starting the burner to burn the fuel gas and oxygen entering the reaction chamber to generate high temperature heat carriers;

b) Feeding the raw gas hydrocarbon feedstock into the reaction chamber from the cracking gas inlet, then the gas hydrocarbon feedstock entering the gas distributor through the gas inlet of the gas distributor, passing through the hollow tubes of the preheating tube from the gas outlet of the gas distributor; the hydrocarbon feedstock being ejected from the upper end of the hollow tube, and then entering the area of the high temperature heat carrier where it is thermally cracked.

c) The thermal cracking product distributing around the hollow tubes of the preheating tubes, and transferring heat to the hollow tubes and to the gas hydrocarbon feedstock which continuously passes through the hollow tubes, thereby continuously heating the gas hydrocarbon feedstock, and the thermally cracking product being finally discharged from the outlet of the reaction chamber.

Further, before step a), the method further includes the steps of preheating the fuel gas and oxygen separately, and then rapidly mixing the fuel gas and oxygen, wherein the temperature at which the fuel gas and oxygen is preheated is in the range of 30° C. to 600° C. Increasing the preheating temperature of fuel gas and oxygen is beneficial for the stability of fuel combustion. It also provides more heat for the subsequent cracking reaction of the cracking gas.

Further, in step b) mentioned above, the mass ratio between the gas hydrocarbon feedstock introduced from the cracking gas inlet and the sum of fuel gas and oxygen injected through the fuel gas inlet is 0.5~1.6. Reducing the mass ratio of gas hydrocarbon feedstock to the sum of fuel gas and oxygen will help increase the thermal cracking reaction temperature and increase the yield of acetylene; while increasing the mass ratio will reduce the thermal cracking reaction temperature and increase the yield of ethylene.

Further, the gaseous fuel in step a) is one or combination of hydrogen, carbon monoxide, methane, and ethane; the hydrocarbon feedstock in step a) is one or combination of methane, ethane, and propane.

Further, the temperature at which the gas hydrocarbon feedstock is preheated in the hollow tubes in step b) is in the range of 200° C. to 600° C. Increasing the initial preheating temperature of the feedstock is beneficial to reducing the heat required for cracking the hydrocarbon feedstock and increasing the yield of ethylene and acetylene.

The advantage of the invention compared to the prior art including: The apparatus of present invention utilizes a combination of a gas distributor and preheating tube to change the direction of the cracking gas entering the heat carrier area from a traditional oblique injecting to a vertical injection, and evenly distributes the cracking gas flow across the entire cross-sectional area of the reaction chamber. The hydrocarbon channel has multiple hollow tubes, which has the following advantages: 1) The hydrocarbon feedstock can be preheated by the cracking reaction product and heat carrier in a high temperature before being injected into the heat carrier area; 2) The cracking gas is injected into the heat carrier area through the hollow tubes connected to the gas distributor and mixed with the heat carrier for cracking reaction; 3) The preheated cracking gas ejected from the ends of multiple hollow tubes forms multiple thermal cracking reaction area in the heat carrier area in the reaction chamber. The scale-up of the reaction chamber is achieved by the method of increasing the number of reaction points, thereby avoiding the problems of incomplete reaction and lower yield due to uneven contact and mixing of the cracking gas and the heat carrier caused by the scale-up of the reaction chamber in the conventional manner.

BRIEF DESCRIPTION OF THE DRAWINGS

These and/or other aspects and advantages of the present invention will become clearer and easier to understand from the following detailed description of the embodiments of the present invention in conjunction with the attached drawings, where.

DETAILED DESCRIPTION OF THE EMBODIMENTS

In order to enable those skilled in the art to better understand it, the present invention is further described in detail below with reference to the accompanying drawings and specific embodiments.

It should be noted that, in the present invention, the "wall of the reaction chamber" includes the top, bottom, and side walls of the reaction chamber, and the "upper part of the reaction chamber" and the "lower part of the reaction chamber" refer to the relative positions up and down in terms of space, which may include walls and internal spaces.

Embodiment 1

Figure 1:
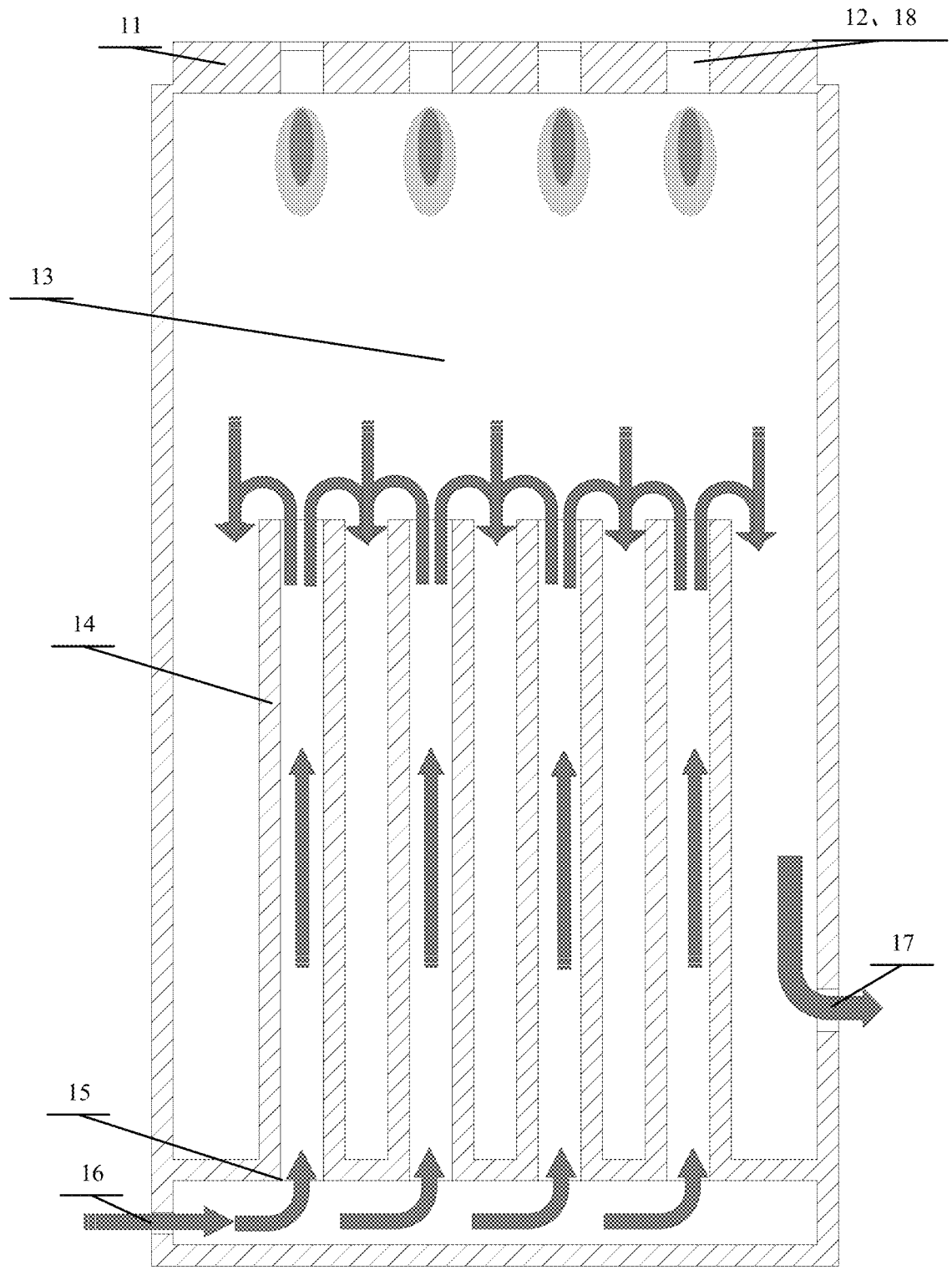
FIG. 1 is a schematic diagram of the structure profile of the apparatus for hydrocarbon production of ethylene and/or acetylene in an embodiment of the invention.
Figure 2:
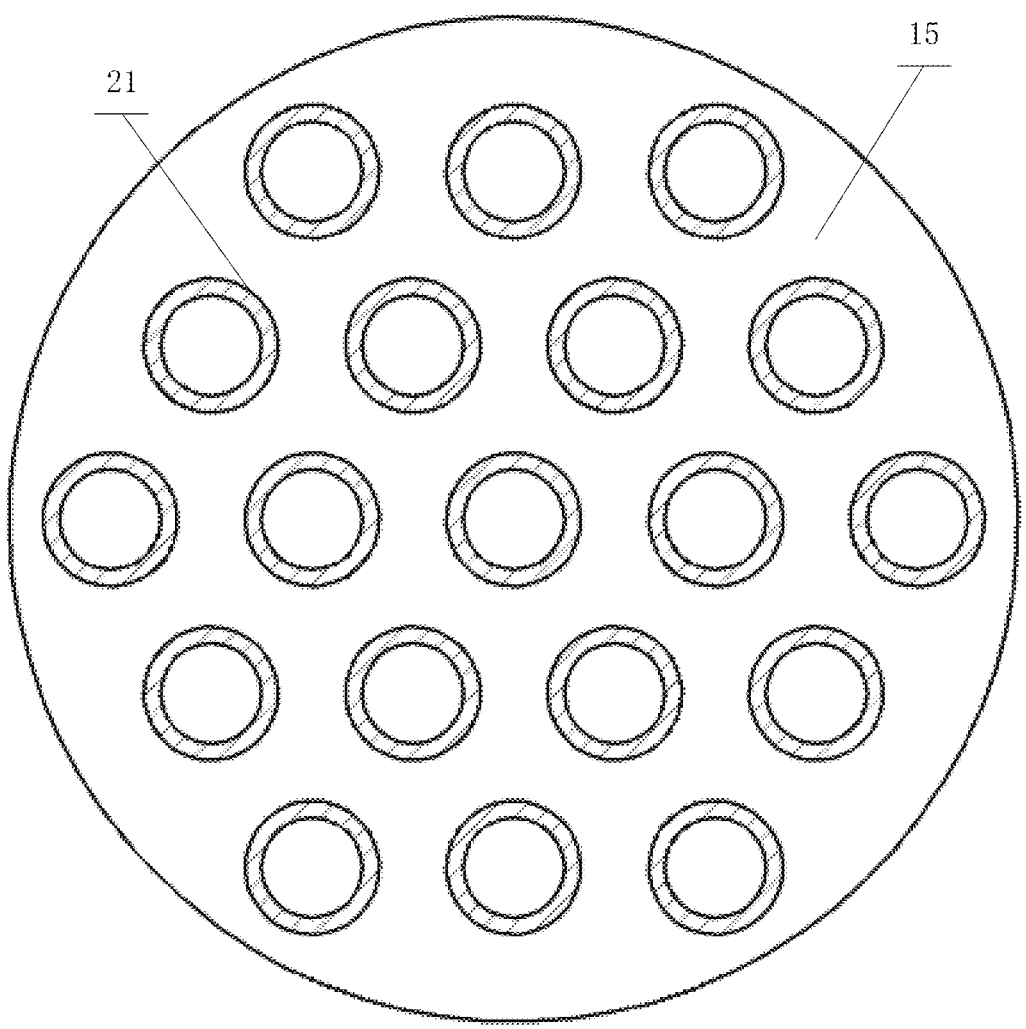
FIG. 2 is a schematic diagram of the gas distributor of the embodiment of the invention.

A structure of an apparatus for producing ethylene and/or acetylene from a hydrocarbon, the sectional view of which is shown in FIG. 1, including chamber 13, preheating tube 14, gas distributor 15, cracking gas inlet 16, and reaction product outlet 17. It can be seen from FIG. 1 that the reaction chamber 13 is a cavity structure in which the reaction feedstock is reacted; The fuel gas inlet 12 and the oxygen inlet 18 are arranged on the top of the reaction chamber 13 and are used to pass the fuel gas and oxygen into the reaction chamber 13. The fuel gas inlet 12 and the oxygen inlet 18 can be arranged in two schemes. One scheme is that one is a fuel gas inlet 12 and the oxygen inlet 18 share one inlet. In this common inlet scheme, the apparatus of this embodiment may include a mixer connected to the front end of the common inlet, so that the preheated fuel gas and oxygen are rapidly mixed in the mixer and then injected into the reaction chamber 13 through a common inlet. The other scheme is that fuel gas and oxygen pass through the reaction chamber 13 through separate inlets. It is preferable that a plurality of common inlets or separate inlets are uniformly arranged on the top wall of the reaction chamber 13 in the two schemes to form a plurality of ignited combustion zones on the cross section of the reaction chamber 13 and finally form a plurality of heat carrier regions; The burner 11 is used to ignite the fuel gas and oxygen, and is also arranged on the top of the reaction chamber 13; The reactant outlet 17 is used to discharge the cracking reaction product out of the reaction chamber 13 and is arranged on the middle side wall of the reaction chamber 12; The gas distributor 15 is arranged on the cross section of the reaction chamber 13 at the lower part of the reaction product outlet 17 and has a gas inlet and a gas outlet. The preferred structure of the gas distributor 15 is a plate provided on the cross section of the reaction chamber 13 so as to isolate the reaction chamber 13 as a whole into upper and lower spaces. As shown in FIG. 2, a plurality of through holes 21 are provided on the plate surface to connect the gas inlet and the gas outlet, so that the upper and lower spaces of the reaction chamber are connected only through the through holes 21; The gas inlet of the gas distributor 15 is connected to the lower space of the reaction chamber 13 where the cracking gas inlet 16 is located. The gas outlet of the gas distributor 15 is located in the upper space of the reaction chamber 13 and is connected to the preheating tube 14. The preheating tube 14 is composed of a plurality of hollow tubes with openings at both ends. The gas outlet of the gas distributor 15 is connected to one end of the hollow tube of the preheating tube 14, and the other end of the hollow tube approaches or are inserted into the heat carrier area formed by combustion of fuel gas and oxygen ignited by the burner 11. In this way, the cracking gas that enters the reaction chamber 13 from the cracking gas inlet 16 is evenly distributed across the cross section of the reaction chamber 13 through the gas inlet of the gas distributor 15, and then passes through the hollow tubes of the preheating tube 14 through the gas outlet. During the reaction, the hollow tube is surrounded by high temperature cracking reaction products, so that the hollow tubes and the cracking gas inside them are continuously heated by the heat of the cracking reaction product. The preheated cracking gas is ejected from the upper end of the hollow tubes, and directly contacts the heat carrier formed by the combustion of fuel gas and oxygen to thermally crack. The solution of this embodiment can be changed as follows: 1) the shape of the through hole 21 is a circle, a square, a triangle, or a pentagon, and the cross-sectional shape of the hollow pipe is a circle, a square, or a triangle. The gas outlet of the through hole can be directly matched with the hollow tubes or connected through a shape adapter. When the cross section of the hollow tubes is circular, the diameter of the hollow tubes is in the range of 5 mm-60 mm, so as to both ensure that the cracking gas forms a sufficient gas flow in the hollow tubes, and also reduce the carbon deposition of the cracking gas in the hollow tubes, which is not easy to clean; 2) the length of the hollow tubes of the preheating tube 14 is set to control the preheating time before the cracking gas is mixed with the heat carrier, wherein the temperature at which the cracking gas is preheated in the hollow tube is generally in the range of 200° C.~600° C., whereby by setting the distance between the preheating tube 14 and the fuel gas and oxygen combustion zone, the reaction temperature of cracking gaseous hydrocarbon can be controlled to some extent; 3) the gas outlet of the gas distributor 15 and its preheating tube 14 are arranged at an angle of 70-110° to the upper and lower bottom surfaces of the reaction chamber 13, and more preferably at 90°.

Embodiment 2

The structure of an apparatus for producing ethylene and/or acetylene from hydrocarbons is basically the same as that of embodiment 1. The difference is that the burner 11, the common or separate fuel gas inlet 12 and the oxygen inlet 18 are arranged at the bottom of the reaction chamber 13, a reaction product outlet 17 is arranged at the lower side wall of the reaction chamber 13, and a cracking gas inlet 16 is arranged at the upper part of the reaction chamber 13. Correspondingly, the gas inlet of the gas distributor 15 faces the top of the reaction chamber 13 and the gas outlet faces the bottom of the reaction chamber 13. The upper end of the hollow pipe of the preheating pipe 14 is connected to the gas outlet of the gas distributor 15, and the lower end is close to or inserted to the heat carrier area formed by the combustion of fuel gas and oxygen in the lower part of the reaction chamber 13. It can be seen that, in this embodiment, the cracking gas hydrocarbon is injected downward in the reaction chamber.

Embodiment 3

A method for producing ethylene and/or acetylene from a hydrocarbon utilizes the apparatus for producing ethylene and/or acetylene from a hydrocarbon of embodiment 1 or 2 and includes the following steps:

a) Injecting fuel gas and oxygen into the reaction chamber 3 through common or separate fuel gas inlet 12 and oxygen inlet 18; Starting the burner 11 to burn the fuel gas and oxygen entering the reaction chamber 13 to generate a high-temperature heat carrier; Preferably, in the scheme of using a common inlet for the fuel gas inlet and the oxygen inlet, the fuel gas and oxygen being preheated separately before injecting into the reaction chamber 13, and then the fuel gas and oxygen being quickly mixed in a mixer preferably provided in the apparatus. In operations that include preheating fuel gas and oxygen, the temperature at which the fuel gas and oxygen are preheated is in the range from 30° C. to 600° C.; Wherein the fuel gas is one or combination of hydrogen, carbon monoxide, methane, and ethane;

b) Feeding the raw gas hydrocarbon feedstock (that is the cracking gas being one or combination methane, ethane, and propane; the mass flow rate of which is preferably has a mass ratio of 0.5~1.6 with respect to the sum of the fuel gas and oxygen injected through the fuel gas inlet 12 in step a), which is controlled by the injection speed and time) into the reaction chamber 13 from the cracking gas inlet 16, and it passing through the gas distributor 15 through its gas inlet, and then it entering the hollow tube of the preheating tube 14 from the gas outlet of the gas distributor 15; The hollow tube transferring the heat of the surrounding cracking products to the gas hydrocarbon feedstock in the hollow tubes; After being preheated, the raw material gaseous hydrocarbons being ejected from the upper end of the hollow tubes, then entering the high-temperature heat carrier area for thermally cracking;

c) The cracking reaction product distributing around the hollow tubes of the preheated tube 14, and transferring the heat to the hollow tubes and to the gas hydrocarbon feedstock which continuously flow into the hollow tubes; The thermally cracking product being finally discharged out of the reaction chamber 13 from the reaction product outlet 17.

Embodiment 4

The reaction chamber 13 is designed 390 mm in diameter (suitable for practical industrial applications). The hollow tubes of the preheating tube 14 have an inner diameter of 15 mm, an outer diameter of 20 mm, and a length of 1000 mm. When the hollow tubes are perpendicular to the bottom of the reaction chamber, the fuel gas (Coke oven gas) and oxygen are preheated to 600° C. separately, and the ratio is the stoichiometric ratio at complete combustion. The fuel gas and oxygen are rapidly mixed and injected into the reaction chamber 13 at a speed of 100 m/s. The cracking gas, ethane, is injected from the bottom of the reaction chamber 13, and the mass ratio between ethane and the sum of coke oven gas and oxygen is 1.3, and the preheating temperature is also 600° C. When the combined yield of acetylene and ethylene reaches its maximum, the yield of acetylene is 21%, the yield of ethylene is 44%, the combined yield of acetylene and ethylene is 65%, the yield of CO is 23%, and the conversion of ethane is 97%. The selectivity to acetylene and ethylene is 66%. The results obtained in the 390 mm large-diameter reaction chamber are basically the same as those in the 30 mm small-diameter reaction chamber, which proves that the reaction chamber designed by the present invention using the numbering up method does not have a scale-up effect, and can be used to scale up the ethane cracking reaction chamber. Correspondingly, in a traditional Jet-In-Cross-Flow reactor, ethane is injected into the reactor from the side of the reactor. In a 30 mm diameter Jet-In-Cross-Flow reactor, the results of ethane cracking are similar to the results of this example, but when the Jet-In-Cross-Flow reactor is enlarged to the size of an industrial reactor of 390 mm, the combined yield of acetylene and ethylene decreases from 65% to 48%, and the reactor scale-up effect is obvious.

Embodiment 5

The hydrocarbon feedstock is pure methane. The diameter of the reaction chamber 13 is 390 mm (suitable for practical industrial applications). The hollow tubes of the preheated tube 14 has an inner diameter of 15 mm, an outer diameter of 20 mm, and a length of 1000 mm. The hollow tubes are perpendicular to the bottom surface of the reaction chamber 13, and the fuel gas (coke oven gas) and oxygen are preheated to 600° C. separately, and the ratio is the stoichiometric ratio at complete combustion. After rapid mixing, it is injected into the reaction chamber 13 at a speed of 100 m/s. The cracking gas, methane, is injected from the bottom of the reaction chamber 13. The mass ratio between methane to the sum of coke oven gas and oxygen is 0.6, and the preheating temperature is also 600° C. When the acetylene yield reaches its maximum, the acetylene yield is 46%, the ethylene yield is 1%, the combined yield of acetylene and ethylene is 47%, the methane conversion is 78%, and the selectivity to acetylene and ethylene is 60%. The results in the 390 mm large diameter reactor are basically consistent with the results in the 30 mm small diameter reactor, which proves that the reactor designed by the method of the present invention does not have an scale-up effect and can be used for the scale-up of a methane cracking reactor. This corresponds to the fact that in a traditional Jet-In-Cross-Flow reactor, methane is injected from the side of the reactor. In a 30 mm diameter Jet-In-Cross-Flow reactor, the maximum combined yield of acetylene and ethylene is 41%, which is lower than the corresponding yield of the reactor structure in the present invention. In the industrial applications, methane is produced by partial oxidation with acetylene. In this method, the yield of acetylene is 31%, which is much lower than the yield of acetylene in the present invention.

The embodiments of the present invention have been described above, the above description is exemplary, not exhaustive, and is not limited to the disclosed embodiments. Many modifications and variations will be apparent to those skilled in the art without departing from the scope and spirit of the various embodiments described. Therefore, the protection scope of the present invention shall be subject to the protection scope of the claims.

What is claimed is:

1. An apparatus for producing ethylene and/or acetylene from hydrocarbon, the apparatus comprising: a reaction chamber (13), a burner (11), common or separate gaseous fuel inlets (12) and oxygen inlets (18), preheating tubes (14), a gas distributor (15), a cracking gas inlet (16), and a reaction product outlet (17);

the reaction chamber (13) being a cavity structure, in which feedstock is reacted; the burner (11), the gaseous fuel inlets (12), the oxygen inlets (18), the cracking gas inlets (16), and the reaction product outlet (17) being set on the wall of the reaction chamber, and the preheating tubes (14) and the gas distributor (15) being arranged in the reaction chamber;

the gaseous fuel inlets (12) being used to feed gaseous fuel into the reaction chamber (13); the oxygen inlets (18) being used to feed oxygen into the reaction chamber (13); the burner (11) being used to ignite the gaseous fuel and the oxygen; the reaction product outlet (17) being used to discharge cracking product out of the reaction chamber (13); the cracking gas inlets (16) being used to feed cracking gas into the reaction chamber (13);

the gas distributor (15), which has multiple gas inlets and gas outlets, being arranged on cross section of the reaction chamber (13), the gas inlets being connected to the cracking gas inlet (16) and the gas outlets being connected to the preheating tubes (14), the gas distributor (15) being used to make the cracking gas, which is fed through the cracking gas inlet (16), uniformly distribute on the cross section of the reaction chamber (13) and pass through the preheating tubes (14);

the preheating tubes (14) including a plurality of hollow tubes having openings at both ends: one opening being connected to gas outlet on the gas distributor (15), and the other opening being located in a combustion zone of the gaseous fuel and the oxygen, the preheating tubes (14) being used to pre-heat the cracking gas uniformly distributed by the distributor (15) and feed the pre-heated cracking gas to the combustion zone of the gaseous fuel and the oxygen, wherein during the cracking reaction, the reaction product is distributed around the hollow tubes to pre-heat the cracking gas in the hollow tubes.

2. The apparatus for producing ethylene and/or acetylene from hydrocarbon as claimed in claim 1, wherein the gas outlets of the gas distributor (15) and the hollow tubes connecting thereto are uniformly distributed in the cross section of the reaction chamber (13).

3. The apparatus for producing ethylene and/or acetylene from hydrocarbon as claimed in claim 1, wherein the gaseous fuel inlets (12) and oxygen inlets (18) are arranged on the top of the reaction chamber (13), and the cracking gas inlet (16), the gas distributor (15) and the preheating tubes (14) are arranged at the lower part of the reaction chamber.

4. The apparatus for producing ethylene and/or acetylene from hydrocarbon as claimed in claim 1, wherein the gaseous fuel inlets (12) and oxygen inlets (18) are arranged at the bottom of the reaction chamber (13), and the cracking gas inlet (16), the gas distributor (15) and the preheating tubes (14) are arranged on the upper part of the reaction chamber.

5. The apparatus for producing ethylene and/or acetylene from hydrocarbon as claimed in claim 1, wherein the gaseous fuel inlets (12) and the oxygen inlets (18) are common inlets, and after being premixed, the gaseous fuel and oxygen are fed into the reaction chamber (13) through the common inlets.

6. The apparatus for producing ethylene and/or acetylene as claimed in claim 5, further comprising a mixer connected to the common inlets of the gaseous fuel inlets (12) and the oxygen inlets (18); the mixer being used to mix the separately pre-heated gaseous fuel and oxygen and inject them into the reaction chamber (13).

7. The apparatus for producing ethylene and/or acetylene from hydrocarbon as claimed in claim 1, wherein the gaseous fuel inlets (12) and the oxygen inlets (18) are independent inlets, and the gaseous fuel and the oxygen enter the reaction chamber (13) through the gaseous fuel inlets (12) and oxygen inlets (18), respectively.

8. The apparatus for producing ethylene and/or acetylene from hydrocarbon as claimed in claim 1, wherein the gas distributor (5) has a plate shape and has a plurality of through holes (21) connecting with the gas inlets and gas outlets; the through holes (21) are evenly distributed on the whole plate of the cracking gas distributor (15), and each of the through holes (21) is connected to a hollow tube.

9. The apparatus for producing ethylene and/or acetylene from hydrocarbon as claimed in claim 8, wherein the through holes (21) is of circle, square, triangle, or pentagon shape, and the cross-section of the hollow tubes is of circle, square, triangle, or pentagon shape.

10. The apparatus for producing ethylene and/or acetylene from hydrocarbon as claimed in claim 8, wherein the cross section of the hollow tubes is of circular shape, and the diameter of the hollow tube is in the range of 5~60 mm.

11. The apparatus for producing ethylene and/or acetylene from hydrocarbons as claimed in claim 1, wherein the common or separate gaseous fuel inlets (12) and oxygen inlets (18) are uniformly distributed on the top or bottom of the reaction chamber (13), so that the gaseous fuel and the oxygen form multiple heat carrier areas on the cross-section of the reaction chamber (13).

12. The apparatus for producing ethylene and/or acetylene from hydrocarbon as claimed in claim 1, wherein each hollow tube is provided with a contraction for gas uniform distribution and pressure adjustment.

13. The apparatus for producing ethylene and/or acetylene from hydrocarbon as claimed in claim 12, wherein the contraction is located on the hollow tube and near the gas distributor.

14. A method for producing ethylene and/or acetylene from hydrocarbon, wherein using the apparatus for producing ethylene and/or acetylene from hydrocarbon as claimed in claim 1, the method comprising:
  a) injecting the gaseous fuel and the oxygen into the reaction chamber (13) through the common or separate gaseous fuel inlets (12) and oxygen inlets (18); starting the burner (11) to burn the gaseous fuel and the oxygen entering the reaction chamber (13) to generate a high-temperature heat carrier;
  b) feeding gas hydrocarbon feedstock from the cracking gas inlet (16) into the reaction chamber (13): the gas hydrocarbon feedstock entering the gas distributor (15) through the gas inlet of the gas distributor (15) passing through the hollow tubes of the preheating tubes from the gas outlet of the gas distributor (15), after being pre-heated by the hollow tubes, the gas hydrocarbon feedstock being injected from the other end of the hollow tube, entering the heat carrier area, and being thermally cracked;
  c) thermal cracking product distributing around the hollow tubes of the preheating tubes (14), and transferring heat to the hollow tubes and to the gas hydrocarbon feedstock continuously introduced into the hollow tubes, and the thermal cracking product being finally discharged out of the reaction chamber (13) through the reaction product outlet (17).

15. The method for producing ethylene and/or acetylene from hydrocarbon as claimed in claim 14, further comprising: before the step a), pre-heating the gaseous fuel and the oxygen separately, and then mixing the gaseous fuel and the oxygen, wherein the preheating temperature of the gaseous fuel and oxygen is in a range of 30° C.~600° C.

16. The method for producing ethylene and/or acetylene from hydrocarbon as claimed in claim 14, wherein the mass ratio between the gas hydrocarbon feedstock introduced from the cracking gas inlet (16) in step b) and sum of the injected gaseous fuel and the oxygen in step a) is 0.5~1.6.

17. The method for producing ethylene and/or acetylene from hydrocarbon as claimed in claim 14, wherein the gaseous fuel in step a) is one or a combination of hydrogen, carbon monoxide, methane, and ethane; the hydrocarbon feedstock in step b) is one or a combination of methane, ethane, and propane.

18. The method for producing ethylene and/or acetylene from hydrocarbon as claimed in claim 14, wherein heating temperature of the gas hydrocarbon feedstock in the hollow tubes in the step b) is in a range of 200° C.~600° C.

* * * * *